(12) United States Patent
Bruce et al.

(10) Patent No.: US 6,228,645 B1
(45) Date of Patent: May 8, 2001

(54) PROMOTER ELEMENTS CONFERRING ROOT-PREFERRED GENE EXPRESSION

(75) Inventors: Wesley Bruce; Guihua Lu, both of Urbandale, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 08/996,069

(22) Filed: Dec. 22, 1997

Related U.S. Application Data

(63) Continuation-in-part of application No. 08/649,172, filed on May 17, 1996, now abandoned.

(51) Int. Cl.[7] ........................................................ C12N 5/14
(52) U.S. Cl. .......................... 435/424; 435/419; 435/412; 435/410; 435/6; 435/DIG. 5; 435/DIG. 17; 435/160; 536/24.1; 536/23.6; 436/503; 800/287; 800/290
(58) Field of Search .................................. 435/424, 419, 435/412, 410, 6, DIG. 5, DIG. 17, 160; 536/24.1, 23.6; 436/503; 800/287, 290

(56) References Cited

U.S. PATENT DOCUMENTS 5,589,379   12/1996   Kridl et al. .

OTHER PUBLICATIONS

Oliphant, A.R., C.J., Brandl, and K. Struhl. 1989. Defining the Sequence Specificity of DNA–Binding Proteins by Selecting Binding Sites Form Random–Sequence Oligonucleotides Analysis of Yeast GCN4 Protein. Mol. Cell. Biol., 9(7):2944–2949.

Ko., L.J. and J.D. Engel. 1993. DNA–Binding Specificities of the GAT–A Transcription Factor Family. Mol. Cell. Biol., 13(7):4011–4022.

Shiraishi, H., K. Okada, and Y. Shimura. 1993. Nucleotide Sequences Recognized by the AGAMOUS–MADS Domain of *Arabidopsis–thaliana* Invitro. Plant J., 4(2):385–398.

Huang, H., et al. 1993. Isolation and Characterization of the Binding Sequences for the Product of the Arabidopsis Floral Homeotic Gene AGAMOUS. Nucleic Acids Res., 21(20):4769–4776.

DeFramond, et al. 1991. A Metallothionein–Like Gene from Maize (*Zea mays*). Cloning and Characterization. FEBS Letters, 290:103–106.

John, et al. 1992. An mRNA Subset That Specifically Accumulates in Maize Roots Delineates a Novel Subset of Developing Cortical Cells. Plant Mol. Biol., 20:821–831.

Held, et al. 1993. An mRNA Putatively Coding for an O–Methyltransferase Accumulates Preferentially in Maize Roots and is Located Predominantly in the Region of the Endodermis. Plant Physiol., 102:1001–1008.

Rigau, et al. 1993. Analysis of Maize α–Tubulin Gene Promoter by Transient Expression and in Transgenic Tobacco Plants. Plant J., 4:1043–1050.

Chevalier, et al. 1995. Molecular Cloning and Characterization of Six cDNAs Expressed During Glucose Starvation in Excised Maize (*Zea mays* L.) Root Tips. Plant Mol. Biol., 28:473–485.

Weising, K. and G. Kahl. 1991. Towards an Understanding of Plant Gene Regulation—The Action of Nuclear Factors. Z. Naturforsch C., 46(1–2):1–11.

Oeda, K., J. Salinas, and N.H. Chna. 1991. A Tobacco bZip Transcription Activator (TAF–1) Binds to a G–Box–Like Motif Conserved in Plant Genes. EMBO J., 10(7):1793–1802.

Takatsuji, H., et al. 1992. Characterization of a Zinc Finger DNA–Binding Protein Expressed Specifically in Petunia Petals and Seedlings. EMBO J., 11(1):241–249.

Yanagisawa, S. and K. Izui. 1992. MNF1, a Leaf Tissue–Specific DNA–Binding Protein of Maize, Interacts with the Cauliflower Mosaic Virus 35S Promoter s Well as the C(4) Photosynthetic Phosphoenolpyruvate Carboxylase Gene Promoter. Plant Mol. Biol., 19(4):545–553.

Zhou, D. X., et al. 1992. Sequence–Specific Interaction Between SlF, a Spinach Nuclear Factor, and a Negative Cis–Element Conserved in Plastid–Related Genes. J. Biol. Chem., 267(33):23515–23519.

Consonni, G., et al. 1993. Molecular Homology Among Members of the R–Gene Family in Maize. Plant J., 3(2):335–346.

Foley, R. C., et al. 1993. Isolation of a Maize bZIP Protein Subfamily—Candidates for the Ocs–Element Transcription Factor. Plant J., 3(5):669–679.

Matsuoka, M., et al. 1993. Tissue–Specific Light–Regulated Expression Directed by the Promoter of a C4 Gene, Maize Pyruvate, Orthophosphate Dikinase, in a C3 Plant, Rice, Proc. Natl. Acad. Sci. USA., 90(20):9586–9590.

(List continued on next page.)

*Primary Examiner*—T. Wessendorf
(74) *Attorney, Agent, or Firm*—Pioneer Hi-Bred International, Inc.

(57) ABSTRACT

This invention relates generally to mechanisms of gene expression in plants and more specifically to regulation of expression of genes in plants in a "tissue-preferred" manner. A method for isolation of transcriptional regulatory elements that contribute to tissue-preferred gene expression is disclosed. Transcriptional regulatory elements isolated using the methods of this invention are demonstrated to direct tissue-preferred gene expression of genes within certain tissues of a plant. DNA molecules representing tissue-preferred transcriptional regulatory elements, vectors containing said DNA molecules and plants transformed with said vectors are demonstrated. Said transcriptional regulatory units are utilized to drive tissue-preferred expression of a gene that confers a selective advantage upon a plant.

2 Claims, 12 Drawing Sheets

OTHER PUBLICATIONS

Norton, G. Agricultural Development Paths and Pest Management—A Pragmatic View of Sustainability, in Crop Protection and Sustainable Agriculture., D.J. Chadwick and J. Marsh, Editor. 1993, John Wiley & Sons Ltd: Baffins Lane, Chichester PO19 7UD, United Kingdom. pp. 100–115.

Liang, P. and A.B. Pardee. 1992. Differential Display of Eukaryotic Messenger RNA by Means of the Polymerase Chain Reaction. Science., 257(5072):967–971.

Bauer, D., et al. 1993. Identification of Differentially Expressed Messenger RNA Species by an Improved Display Technique (DDRT–PCR). Nucleic Acids Res., 21(18):4272–4280.

Godowski, P.J., D. Picard, and K.R. Yamamoto. 1988. Signal Transduction and Transcriptional Regulation by Glucocorticoid Receptor–LexA Fusion Proteins. Science., 241:812–816.

Norby, P.L., et al. 1992. Determination of Recognition–Sequences for DNA–Binding Proteins by a Polymerase Chain Reaction Assisted Binding Site Selection Method (BSS) Using Nitrocellulose Immobilized DNA Binding Protein. Nucleic Acids Res., 20(23):6317–6321.

Catron, K.M., N. Iller, and C. Abate. 1993. Nucleotides Flanking a Conserved TAAT Core Dictate the DNA Binding Specificity of 3 Murine Homeodomain Proteins. Mol. Cell Biol., 13(4):2354–2365.

Lissemore, J. and P.H. Quail. 1988, Rapid Transcriptional Regulation by Phytochrome of the genes for Phytochrome and Chlorophyll a/b–Binding Protein in *Avena Sativa*. Mol. Cell Biol., 8:4840–4850.

Yanagisawa, S. and K. Izui. 1993. Molecular Cloning of 2 DNA–Binding Proteins in Maize that are Structurally Different but Interact with the Same Sequence Motif. J. Biol. Chem., 268(21):16028–16036.

Schmidt, R.J., et al. 1992. Opaque–2 Is a Transcriptional Activator That Recognizes a Specific Target Site in 22–kD–Zein Genes. Plant Cell., 4(6):689–700.

Kano, M.Y., et al. 1991. Sequence–Specific Interactions of a Maize Factor with a BC–Rich Repeat in the Phosphoenolpyruvate Carboxylase Gene. Mol. Gen. Genet., 225(2):203–208.

Oliphant, A.R., A.L. Nussbaum, and K. Struhl. 1986. Cloning of Random–Sequence Oligodeoxynucleotides. Gene (Amst)., 44(2–3):177–184.

O'Farrell, P.H. 1975. High Resolution Two–Dimensional Electrophoresis. J. Biol. Chem. 250:4007–4021.

Baszczynski, C.L., D.B. Walden, and B.G. Atkinson. 1985. Maize Genome Response to Thermal Shifts in Changes in Eukaryotic Gene Expression in Response to Environmental Stress. pp. 349–371.

Ehrlich, K.C. 1993. Partial Purification of a Pea Seed DNA–Binding Protein that Specifically Recognizes 5–Methylcytosine. Prep. Biochem., 23(4):423–438.

Meller, Y., et al. 1993. DNA–Protein Interactions on a cis–DNA Element Essential for Ethylene Regulation. Plant Mol. Biol., 23(3):453–463.

Berthomieu, P. and C. Meyer. 1991. Direct Amplification of Plant Genomic DNA from Leaf and Root Pieces Using PCR. Plant Mol. Biol., 17(3):555–557.

Ouellette, M.M., Chen, J., Wright, W.E., and J.E. Shay. 1992. Complexes Containing the Retinoblastoma Gene Product Recognize Different DNA Motifs Related to the E2F Binding Site. Oncogene., 7:1075–1081.

Lam, et al. 1989. Site–Specific Mutations Alter in vitro Factor Binding and Change Promoter Expression Pattern in Transgenic Plants. Proc. Natl. Acad. Sci. USA., 86:7890–7894.

Malik, K.F. et al. 1996. Binding Preferences of the POR domain protein Brain–4: Implications for Autoregulation. Molec. Brain Res., 38(2):209–221.

Seyfert, et al. 1996. Transcriptional Repression by the Proto–Oncogene BCL–6. Oncogene., 12(11):2331–2342.

Shore, P. and A.D. Sharrocks. 1995. The ETS–Domain Transcription Factors Elk–1 and SAP–1 Exhibit Differential DNA Binding Specificities. Nuc. Acids Res., 23(22):4698–4706.

Jellinek, D., et al. 1995. Potent 2'Amino–1'Deoxypyrimidine RNA Inhibitors of Basic Fibroblast Growth Factor. Biochemistry., 34(36):11363–11372.

Huang, et al. 1995. The Arabidopsis MADS–Box Gene AGL3 is Widely Expressed and Encodes a Sequence–Specific DNA–Binding Protein. Plant Mol. Biol., 28(3):549–567.

Nallur, et al. 1996. Multiplex Selection Technique (MuST): An Approach to Clone Transcription Factor Binding Sites. Proc. Natl. Acad. Sci. USA., 93:1184–1189.

Gold, L. 1995. Oligonucleotides as Research, Diagnostic, and Therapeutic Agents. J. Biol. Chem., 270:13581–13584.

Gold, L. 1995. Diversity of Oligonucleotide Functions. Ann. Rev. Biochem., 64:793–797.

Thiesen et al. 1990. Target Detection Assay (TDA): A Versatile Procedure to Determine DNA Binding Sits as Demonstrated on SP1 Protein. Nuc. Acids Res., 18(11):2303–3209.

Lerchl et al., Molecular Cloning, Characterization and Expression Analysis of Isoforms Encoding Tonoplast Bound Proton Translocating Inorganic Pyrophosphatase in Tobacco. EMBL Seq. Data Library, Apr. 1995, XP002042002, Accession No. X83728.

PROMOTER ELEMENTS CONFERRING ROOT-PREFERRED GENE EXPRESSION

This application is a continuation-in-part of application Ser. No. 08/649,172, filed May 17, 1996, abandoned.

BACKGROUND OF THE INVENTION

1. Field of the Invention

This invention relates generally to mechanisms of gene expression in plants and more specifically to regulation of expression of genes in plants in a "tissue-preferred" manner. A method for isolation of transcriptional regulatory elements that contribute to tissue-preferred gene expression is disclosed. Transcriptional regulatory elements isolated using the methods of this invention are demonstrated to direct tissue-preferred gene expression of genes within certain tissues of a plant. DNA molecules representing tissue-preferred transcriptional regulatory elements and vectors comprising said DNA molecules are demonstrated. Said transcriptional regulatory unit will ultimately be utilized for driving tissue-preferred expression of at least one gene that confers a selective advantage upon a plant.

2. Description of the Related Art

Gene expression encompasses a number of steps from the DNA template to the final protein or protein product. Initiation of transcription of a gene is generally understood to be the predominant controlling factor in determining expression of a gene. The transcriptional controls are generally relegated to relatively short sequence elements embedded in the 5'-flanking or upstream region of the transcribed gene to which DNA-binding proteins may interact. These DNA sequence elements serve to promote the formation of transcriptional complexes and eventually initiate gene expression processes. A number of labs have identified promoter elements and corresponding DNA-binding proteins that are limited to specific tissues within the plant (Weising, et al Z. Naturforsch C46:1; Oeda, et al EMBO J. 10:1793; Takatsuji, et al EMBO J 11:241; Yanagisawa, et al Plant Mol. Biol. 19:545; Zhou, et al J. Biol. Chem. 267:23515; Consonni, et al Plant J. 3:335; Foley, et al Plant J. 3:669; Matsuoka, et al Proc. Natl. Acad. Sci. 90:9586). It is likely that a large number of DNA-binding factors will be limited to specific tissues, environmental conditions or developmental stages. It is considered important by those skilled in the art to develop transcriptional regulatory units that restrict gene expression to certain tissues of a plant. The ability to drive tissue-specific gene expression in plants is considered to be of agronomic importance to those skilled in the art.

Controlling the expression of agronomic genes in transgenic plants is considered by those skilled in the art to provide several advantages over generalized or constitutive expression. The ability to control gene expression may be utilized to exclude expression in germline tissues thus avoiding certain regulatory and commercial issues. It can also provide a pest refugia in the case of insect and disease resistance, a preferred pest management strategy (Norton, G., *Agricultural Development Paths and Pest Management—A Pragmatic View of Sustainability, in Crop Protection and Sustainable Agriculture,* 1993, p. 100–115), and it can reduce potential yield loss by limiting expression of some pernicious, yet useful agronomic genes to only specific tissues. Further advantages of utilizing promoters that function in a tissue-preferred manner include reduced resource drain on the plant in making a gene product constitutively, as well as localization or compartmentalization of gene expression in cases where the gene product must be restricted to, or from, a certain tissue. Said gene products may include general cellular inhibitors such as RNases or other cytotoxins. As an example, Mariani, et al (Nature 347:737, 1990) demonstrated anther-specific gene expression of suc inhibitor genes for use in male sterility systems, since expression in regions other than the anther in a plant would be toxic. There is a need in the art for novel transcriptional regulatory elements capable of driving tissue-preferred gene expression in plants. It is considered important by those skilled in the art to continue to provide tissue-preferred transcription units capable of driving expression of genes that may confer a selective advantage to a plant.

It is also considered important to those skilled in the art to develop transcriptional regulatory units that direct gene expression selectively to root tissue. Root-preferred gene expression will provide several advantages to a plant including but not limited to alteration of the growth rate or function of the root tissue, resistance to root-preferred pathogens, pests, herbicides or adverse weather conditions as well as broadening the range of soils or environments in which said plant may thrive. Root-preferred gene expression would also provide a mechanism by which root morphology and metabolism may be altered to improve yield (i.e., direct expression of transporter proteins). Further advantages to root-preferred gene expression include the production of useful proteins in an industrial setting. Light-sensitive proteins may be synthesized in root tissue such that said proteins are not exposed to light.

A promoter element or elements that specifically confer root-preferred expression has not been described. Short elements that may contribute to root-preferred expression have been disclosed; however, identification of the specific sequences responsible for root-specific gene expression have not been reported (Lam, et al. 1989. Proc. Natl. Acad. Sci. USA 86:7890). Importantly, most of the disclosed elements are derived from dicots not from monocots (as was this invention). Based on what is known by those skilled in the art, it is unlikely that a dicot promoter sequence will function properly in a monocot.

Approaches that may be utilized to isolate tissue-specific transcriptional control elements include differential or subtractive cDNA cloning followed by cloning of the genomic 5'-flanking sequence comprising the promoter elements responsible for tissue-preferred gene expression. A recently developed technique, differential display analysis (Liang, et al Science 257:967; Bauer, et al Nuc. Acids Res. 21:4272), involves PCR-based identification of differentially expressed genes as partial cDNAs. A major drawback to the techniques taught in the prior art is that cloning of full length cDNA and genomic sequences as well as mapping of the identified promoter from genomic clones may be required. These techniques potentially require a multiple-year project with minimal returns on investment. The present invention, which is a subject of this application, addresses these issues by providing a methodology that allows for rapid isolation, identification and utilization of DNA elements that drive tissue-preferred gene expression.

This invention teaches a process of enrichment of novel DNA sequences that interact with tissue-specific DNA-binding proteins. DNA sequences so isolated may then be utilized to construct expression vectors useful in driving tissue-specific gene expression within transgenic tissues or organisms. A random oligonucleotide library (ROL) is designed and applied to a crude mixture of nuclear proteins from the target tissue (e.g. root) immobilized on a filter (designated as a Southwestern assay). The bound ROL are eluted and applied to an immobilized, crude mixture of nuclear proteins from the non-target tissue (e.g. leaf). Non-bound ROL are then PCR-amplified and the entire cycle repeated to further enrich for DNA sequences that bind to nuclear proteins from the target tissue (e.g. root). The use of ROL's binding directly to crude nuclear extracts in a subtractive enrichment process for generating a library of tissue (or developmental or environmental state)-specific promoter elements has not been described.

As demonstrated by Oliphant, et al. (Mol. Cell. Biol. 9:2944), ROL's have been utilized to identify alternative DNA recognition sequences of DNA-binding proteins. Variations of this technique have also been used to identify alternative sequence recognition of specific DNA-binding factors (Norby, et al Nuc. Acids Res. 20:6317; Catron, et al Mol. Cell. Biol. 13:2354; Ko, et al Mol. Cell. Bill. 13:4011; Shiraishi, et al Plant J. 4:385; Huang, et al Nuc. Acids Res. 21:4769). The technique of applying crude nuclear extracts to an ROL was successfully utilized to identify several oligonucleotides that bind to retinoblastoma tumor-suppressor gene products (Ouellette, et al. Oncogene 7:1075–1081). In each of the above-described techniques, however, a purified DNA-binding factor or antibody specific for a DNA binding factor is required. This invention teaches the isolation of tissue-specific oligonucleotides from a pool of random sequences using a heterogeneous mix (crude extract) of nuclear proteins without the need for either a purified protein or an antibody of any sort. The enriched collection of oligonucleotides are then isolated, cloned into expression vectors, and tested for the ability to drive tissue-specific gene expression. Importantly, the invention of the present application provides a significant methodological advancement over previously described techniques and is applicable to any plant or non-plant tissue that is amenable to nuclear extract preparation.

SUMMARY OF THE INVENTION

This invention provides a method for the isolation of transcriptional regulatory elements that contribute to the tissue-preferred patterns of certain genes. Tissue-preferred gene expression includes but is not limited to gene expression observed solely or preferably in certain tissues, environmental situations and during certain stages of development. The invention further provides a method for isolation of transcriptional regulatory elements that contribute to root-tissue specific gene expression in maize. Transcriptional regulatory elements and expression vectors comprising said transcriptional regulatory elements are disclosed. Said transcriptional regulatory elements drive root-tissue preferred gene expression in transgenic plants. Said transcriptional regulatory elements are utilized to generate expression vectors comprising a transcriptional regulatory region that includes a tissue-preferred element isolated by the methods of this invention operably linked to an effector gene that, upon expression of the protein product of said effector gene, confers a selective advantage to plants. Said selective advantage may include, but is not limited to resistance to pests, pathogens, herbicides, or adverse weather conditions as well as effects on growth, yield or reproductive capacities of said plants.

It is an object of this invention to provide a method for isolation of transcriptional regulatory elements representing a transcriptional regulatory region of a gene expressed in a tissue specific manner.

It is another object of the invention to provide DNA molecules representing genes or fragments thereof that are expressed in a tissue-preferred manner.

It is yet another object of the invention to provide DNA molecules representing an element of a transcriptional regulatory region of a gene that is expressed in a tissue-preferred manner.

It is also an object of the invention to provide reporter constructs useful for testing the ability of a potentially tissue-preferred transcriptional regulatory element to drive expression of a reporter gene in a tissue-preferred manner in vivo.

It is another object of the invention to provide a method useful for testing the ability of said transcriptional regulatory region to drive expression of a reporter gene in a tissue-preferred manner in vivo.

It is a further object of the invention to provide DNA molecules comprising a tissue-specific promoter element or elements operably linked to an effector gene that, upon expression of the polypeptide product of said effector gene, will confer a selective advantage to a plant transformed said DNA molecule.

In one embodiment of the invention, a random oligonucleotide library of the general sequence illustrated in SEQ ID NO:1 is provided.

In another embodiment of the invention, a random oligonucleotide library of the general sequence illustrated in SEQ ID NO:2 is provided.

In still another embodiment of the invention, an oligonucleotide of the sequence illustrated in SEQ ID NO:3 is provided.

In another embodiment of the invention, an oligonucleotide of the sequence illustrated in SEQ ID NO:4 is provided.

In one embodiment of the invention an isolated and purified subchromosomal DNA molecule as shown in SEQ ID NO:5 is provided.

In another embodiment of the invention an isolated and purified subchromosomal DNA molecule as shown in SEQ ID NO:6 is provided.

In another embodiment of the invention a method is provided whereby a transcriptional regulatory element is isolated by incubating of a random oligonucleotide library with a first nuclear extract of a cell or tissue, isolating of bound oligonucleotides, hybridizing said oligonucleotides to a second nuclear extract of a cell or tissue-type other than that utilized for the initial hybridization, and isolating those oligonucleotides that do not bind to said second nuclear extract. The entire cycle is then repeated resulting in the isolation of a group of an oligonucleotide or oligonucleotides that preferably bind to said first nuclear extract.

In yet another embodiment of the invention, expression vectors in which tissue-preferred expression of an assayable gene product is controlled by the seq6 transcriptional regulatory element are provided as shown in FIGS. 6 and 10.

These and other objects of the invention will be apparent to those skilled in the art from the following detailed description of a preferred embodiment of the invention.

DETAILED DESCRIPTION OF THE INVENTIONS

Figure 1:
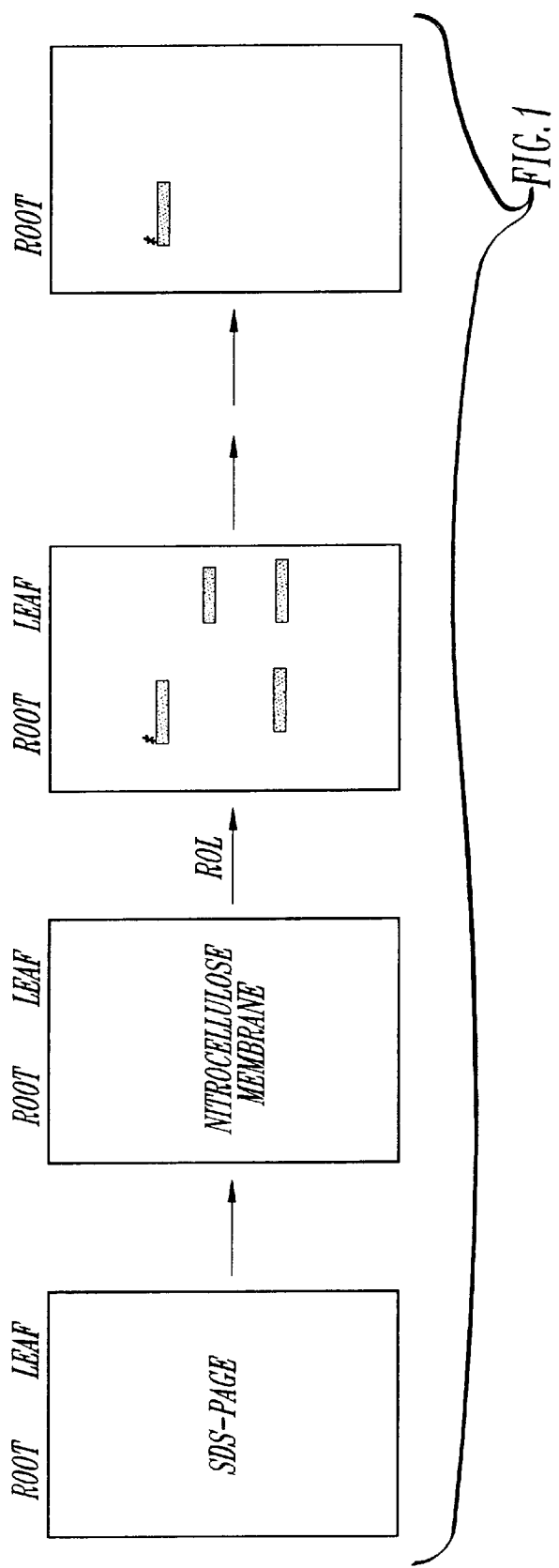
FIG. 1. Procedure for isolation of root-preferred transcriptional regulatory elements using a modifed version of the Southwestern blot assay.

Within this application, plant refers to a photosynthetic organism including algae, mosses, ferns, gymnosperms, and angiosperms.

A plant cell includes any cell derived from a plant, including callus as well as protoplasts, and embryonic and gametic cells.

A mature plant is defined as a plant in which normal development of all vegetative and reproductive organs has occurred.

Transgenic plant defines a plant in which a gene has been added to the germline of said plant.

Transformation refers to a method of introduction of DNA into a cell. Said introduction may include but is not limited to particle bombardment, lipofection, electroporation, viral or bacterial vector-mediated, and calcium phosphate mediated techniques.

A gene product that confers a selective advantage to a plant is defined as any gene product which, upon expression in said plant, confers a characteristic on a plant including but not limited to increased growth rate, yield of product or resistance to threats to said plant's ability to thrive including but not limited to pathogens, pests, adverse weather conditions, and herbicides relative to plants that do not express said gene product.

A DNA fragment is defined as segment of a single- or double-stranded DNA derived from any source including synthetically-produced DNA.

A DNA construct is defined a plasmid, virus, autonomously replicating sequence, phage or linear segment of a single- or double-stranded DNA or RNA derived from any source.

A reporter gene is defined as a subchromosomal and purified DNA molecule comprising a gene encoding an assayable product.

A reporter construct is defined as a DNA construct comprising a reporter gene.

An expression vector is defined as a DNA construct comprising at least one gene which, upon transection into a cell, results in expression of the product of said gene.

An assayable product includes any product encoded by a gene that is detectable using an assay. Furthermore, the detection and quantitation of said assayable product is anticipated to be directly proportional to the level of expression of said gene.

An effector gene is defined as any gene that, upon expression of the polypeptide encoded by said gene, confers an effect on an organism, tissue or cell.

The term operably linked refers to the combination of a first nucleic acid fragment representing a transcriptional control region having activity in a cell joined to a second nucleic acid fragment encoding a reporter or effector gene such that expression of said reporter or effector gene is influenced by the presence of said transcriptional control region.

A transcriptional regulatory region is defined as any region of a gene involved in regulating transcription of a gene, including but not limited to promoters, enhancers and repressors.

A transcriptional regulatory element is defined as any element involved in regulating transcription of a gene, including but not limited to promoters, enhancers and repressors.

Tissue-preferred defines a gene or gene product, expressed in one tissue in a greater amount as opposed to one or more second tissues in an organism or that the fuinction of a certain gene or gene product is optimal in one tissue as opposed to one or more second tissues in an organism. Said tissues may be differentiated by a number of conditions including but not limited to tissue type, developmental stage of a tissue and environmental state of said tissue.

A tissue-preferred promoter element or a tissue-preferred transcriptional regulatory element is defined as a promoter element or transcriptional regulatory region that drives expression of at least one gene in a tissue-preferred manner.

A tissue of different tissue origin is defined as a tissue that may be differentiated from at least one other tissue by at least one of several criteria including but not limited to tissue type, environmental state of said tissue or developmental stage of said tissue.

A regenerable culture is defined as a cell or tissue culture that can be manipulated so as to allow regeneration of plants.

A gene product useful in controlling pests defines any gene that functions to inhibit the growth, migration, existence or behavior of any pest that may threaten the normal life cycle of one or more organisms.

The present invention provides oligonucleotides, transcriptional regulatory elements, expression vectors, transgenic plants and methods that provide for the simple and specific identification of gene promoter elements that contribute to tissue-preferred expression of certain genes. The invention further provides for the development of a library of putative tissue-preferred elements that may be screened to identify both activator and repressor elements from specific tissue types of most any organism. A random oligonucleotide library (ROL) is initially hybridized to a crude nuclear extract containing factors that are selectively present in particular plant tissues. Following repeated hybridizations to both the tissue of interest and a "non-specific" tissue utilized solely to subtract oligonucleotides that bind to nuclear factors of both the tissue of interest and the non-specific tissue, a tissue-preferred ROL is generated. Said tissue-preferred ROL represents putative tissue-preferred promoter elements that bind to nuclear factors of the tissue of interest. The population of putative tissue-preferred promoter elements are then incorporated into expression vectors such that a putative tissue-preferred promoter element is operably linked to a gene encoding an assayable product. Following tranfection into cells or tissue preparations, the ability of a putative tissue-preferred element or elements to drive tissue-preferred gene expression is determined. Certain constructs are then selected for further testing in specific tissue samples, including transgenic organisms.

The prior art teaches limited usage of an ROL in the identification of specific DNA/protein interactions. However, the methods disclosed in the prior art are limited to the use of cloned, purified nuclear proteins as opposed to crude mixtures of nuclear proteins as taught in this invention (Norby, et al Nuc. Acids Res. 20:6317; Catron, et al Mol. Cell. Biol. 13:2354; Ko, et al Mol. Cell. Bill. 13:4011; Shiraishi, et al Plant J. 4:385; Huang, et al Nuc. Acids Res. 21:4769). Ouellette, M. M., et al. (Oncogene 7:1075–1081) teach the application of an ROL to a crude mixture of nuclear proteins to identify oligonucleotides that specifically bind to Rb-family polypeptides. However, an important limitation to the Ouellette, et al. teaching is that an antibody specific to a class of retinoblastoma (Rb) proteins is required to identify those oligonucleotides that specifically bind Rb-family polypeptides. A major disadvantage to the methodologies described in the prior art is that either a cloned, purified nuclear protein or an antibody to a DNA-binding protein is required. Neither a cloned protein nor an antibody of any type is required to utilize the methods taught in the invention disclosed within this application.

Prior to the invention disclosed within this application, it was necessary to identify genes that demonstrate a tissue-preferred pattern of expression in plants in order to isolate transcriptional regulatory regions useful for driving tissue-preferred expression of effector genes in plants. One method of identification is PCR-based differential display analysis (Liang, et al. Science 257:967). This methodology involves the use of random oligonucleotide primers, PCR-amplification of RT-cDNA and comparison of patterns of expression between at least two samples. Said samples may include but are not limited to different types of cells or tissues, cells or tissues in various stages of development, or cells or tissues that have been exposed to various chemicals or conditions and may result in a change in gene expression in said cells or tissues. Non-identical DNA banding patterns of DNA amplified from said samples indicate a difference in gene expression between samples. DNA corresponding to the bands which exhibit said non-identical DNA banding patterns are cloned and utilized to identify the genes to which the DNA bands correspond. An alternative method involves the use of subtractive hybridization (Lee, et al. Proc. Natl. Acad. Sci. 88:2825). This methodology involves the hybridization of cDNA (antisense) of sample A and biotinylated-RNA of sample B. Biotinylated-RNA molecules of sample B representing genes expressed in both samples will hybridize to the complementary cDNA molecules of sample A and will be destroyed by subsequent enzymatic treatment. Following purification of the remaining biotinylated RNA molecules of sample B, a cDNA library is constructed using said remaining biotinylated RNA of sample B. The clones of said cDNA library represent genes that are preferentially expressed in sample B. A further method is by screening of a cDNA library of a first sample using labeled RNA representing a second sample. Clones of said cDNA library of said first sample that do not hybridize to said labeled RNA of said second sample represent mRNA species that are not expressed in said second sample. Alternatively, several libraries may be individually screened using labeled RNA from several separate samples. If said samples are different tissues of a plant, altered patterns of hybridization in one sample as compared to another sample indicates a tissue-preferred pattern of gene expression. cDNA clones isolated in the above-described manner will represent mRNA species that are preferentially expressed in a sample or a group of samples.

It is then necessary to confirm that a cDNA isolated by any of the above-described techniques or any other technique resulting in the isolation of potentially tissue-preferred plant genes is expressed in a tissue-preferred manner. RT-PCR is a method by which mRNA represented by a potentially tissue-preferred cDNA is amplified from a cell or tissue of interest (Berchtold, et al. Nuc. Acids. Res. 17:453). Amplification of said mRNA from several different tissues allows for a comparison to be made and the relative level of expression of mRNA of said potentially tissue-preferred plant gene to be determined. Another method which may be utilized to determine the level of gene expression in a plant cell or plant tissue is RNase protection assays (Melton, et al. Nuc. Acids. Res. 12:7035). RNA from the samples to be compared is hybridized to a labeled antisense RNA probe generated from a cDNA representing a mRNA of a plant gene potentially expressed in a tissue-specific manner. This is followed by the addition of RNase. All RNA which has hybridized to said labeled antisense RNA probe is protected from degradation (termed protected transcripts) by the RNase while mRNA that has not hybridized to said antisense labeled RNA probe is degraded. The products are then separated by gel electrophoresis and protected transcripts detected using detection methods including but not limited to autoradiography. The relative intensity of the band corresponding to said protected transcripts is proportional to the level of expression of that protected RNA species in each tissue. An additional method with which tissue-preferred expression may be determined is by northern blot analysis (Alwine, et al. Proc. Natl. Acad. Sci. 74:5350). RNA isolated from a sample of interest is isolated and separated by gel electrophoresis. The separated RNA species are then transferred to a membrane and probed with a labeled nucleic acid probe that is complementary to RNA representing a gene of interest. Hybridization is detected using a detection method including but not limited to autoradiography. The intensity of the band corresponding to RNA representing a gene of interest is determined and is proportional to the level of gene expression in each sample. A tissue-preferred gene is identified by increased hybridization in one tissue as compared to a second tissue of a plant.

It is then desirable to isolate the transcriptional regulatory region responsible for driving expression of said gene of interest in a tissue-preferred manner. This region may be isolated by several methods including but not limited to amplification of a region of DNA comprising said transcriptional regulatory region. Said DNA is amplified from genomic DNA maintained as a genomic DNA library in a cloning vector including but not limited to phage, plasmids, cosmids, yeast artificial chromosomes (YAC) or any other vector capable of harboring fragments of chromosomal DNA. Said transcriptional regulatory region of said gene expressed in a tissue-preferred manner may be isolated by amplification of the genomic sequences encoding the cDNA sequence. Two oligonucleotide primers, the first of which comprising sequence complementary to a region within the nucleotide sequence of said cloning vector and the second of which comprising sequence complementary to a 5' region of said cDNA encoding a gene expressed in a tissue-preferred manner, are utilized in a PCR reaction. The template for said PCR reaction comprises a portion of said genomic DNA library. Amplification products may include but are not limited to DNA comprising a 5' transcriptional regulatory region of said gene of interest, the remaining 3' sequence of said cDNA including a 3' untranslated region, or fragments thereof. DNA sequencing of each amplified product results in identification of those clones comprising a potential transcriptional regulatory region (Frohman, et al. Proc. Natl. Acad. Sci. 85:8998). A further method for isolation of the transcriptional region of a gene expressed in a tissue-preferred manner includes utilization of the cDNA or fragment thereof encoding the gene of interest as a cDNA probe to screen said genomic DNA library by hybridization. Clones which demonstrate hybridization to said cDNA probe are isolated and characterized by restriction enzyme mapping and nucleotide sequence analysis.

Elements or regions of DNA responsible for tissue-preferred gene expression are isolated using methods including but not limited to the following procedures. Nucleotide sequence and restriction enzyme maps of said genomic clones that demonstrate hybridization to said cDNA probe are determined. Using restriction enzyme digestion and subcloning methods well known to those skilled in the art, expression vectors are constructed comprising various regions of said genomic clone linked in cis to a gene encoding said assayable product to generate an expression vector in which expression of an assayable product is driven by said various regions of said genomic clone. A further method includes the utilization of an oligonucleotide comprising nucleotide sequence complementary to the 5' region of said transcriptional control region of said gene expressed in a tissue-preferred manner and an oligonucleotide comprising nucleotide sequence complementary to a 3' transcriptional control region of said gene expressed in a tissue-preferred manner are synthesized. Preferably, each oligonucleotide further comprises nucleotide sequence corresponding to restriction enzyme sites compatible for cloning into an expression vector encoding an assayable product. Following amplification of DNA comprising the transcriptional control region, cloning of said region into said expression vector is accomplished using techniques well known in the art. Use of the above-described methodologies results in the construction of expression vectors comprising separate potential transcriptional control regions linked in cis to a gene encoding an assayable gene product.

Expression vectors useful for testing a potentially tissue-preferred transcriptional regulatory element or region isolated by any of the methodologies disclosed within this application are then constructed. Said elements are inserted into the transcriptional control region of an expression vector such that said transcriptional control region is operably linked in cis to a gene encoding an assayable product. Said assayable product may include but is not limited to beta-glucuronidase (GUS™), luciferase, beta-galactosidase, green fluorescent protein (GFP) or chloramphenicol transferase (CAT). To confirm that said transcriptional control region functions in a tissue-preferred manner in plant tissues, said expression vector comprising a transcriptional control region of a gene expressed in a tissue-preferred manner in plants operably linked in cis to an assayable product is transfected into plant cells or tissues. The method utilized for transfection of various types of plant cells or plant tissues may include but is not limited to particle bombardment, liposome-mediated transection, calcium phosphate-mediated transection, bacterial- or viral-mediated gene transfer, and electroporation. Said various cells or tissues may be transfected in vitro after excision from said plant. Following a defined period of time after transection of said construct into said tissues, the tissues are harvested and an assay capable of detecting said assayable product is performed. The amount of assayable product detected in said cells or tissues is proportional to the ability of said transcriptional control region to function in that cell or tissue. In this manner, the ability of said transcriptional regulatory region to drive tissue-preferred gene expression is determined. Alternatively, said cells or tissues may be utilized to generate of transgenic plants. Said transgenic plants have at least one copy of said expression vector comprising said transcriptional control region linked in cis to a gene encoding an assayable product incorporated into the genome of the plant. Said copy is therefore present in each cell and tissue of said transgenic plant. Harvest of said tissues is followed by assay of said tissues for expression of said assayable product. The amount of said assayable product in each of said tissues is determined and is proportional to the level of expression of said gene encoding said assayable product in each of said tissues. In this manner, the ability of the transcriptional control region of said cDNA to drive tissue-preferred gene expression is determined.

The ability of said transcriptional control region to drive tissue-preferred expression of genes may also be tested by the generation of transgenic plants in which the transgene comprises a tissue-preferred transcriptional control region driving expression of an effector gene that confers a selective advantage to those plants comprising said transgene. Said transgenic plants are allowed to mature and are then challenged by a pest which may exhibit a response to expression of said effector gene in a plant. Preferably, the pest is selected from a group of pests which are present for at least a portion of their lifespan in a tissue in which said transcriptional control region drives gene expression. The behavior of said pest is demonstrated to be altered in those tissues in which the effector gene is expressed. The change in said behavior of said pest includes but is not limited to altered growth characteristics, inability to thrive, or death.

Said transcriptional control region may also be utilized to drive expression of genes involved in other aspects of plant physiology including but not limited to resistance to pests other than insects, resistance to herbicides, growth of the plant, resistance of fruits or vegetables to spoiling, or resistance to adverse weather conditions. Said pests other than insects may also include but are not limited to bacteria, parasites, fungi, viral agents, and viroids including but not limited to the fungi, fusarium and fumonsin, or the virus known as the Tobacco Mosaic Virus. The growth characteristics of a plant include but are not limited to those that result in the production of increased amounts of fruit, increased amounts of seed, growth at either a faster or a slower rate, or growth in a season other than that considered ordinary for said plant. Adverse weather conditions to which the plant may become resistant include but are not limited to temperatures above or below that which the plant is not ordinarily able to survive, flooding, and drought.

The methodologies disclosed within this application eliminate much of the extensive and time-consuming cloning and mutational analyses necessary for identifying promoter elements as taught in the prior art. In addition, utilization of the methodology of the present invention results in the generation of a library of promoter elements rather than the one or few elements that likely result from utilization of conventional approaches such as those described in the prior art. The methodology of the invention of this application is applicable to any tissue in any developmental or environmentally-induced state that is amenable to nuclear extract preparations.

The following examples illustrate particular embodiments of the present invention and are not limiting of the specification and claims in any way.

EXAMPLE 1

Isolation of Elements that Confer Root-Preferred Gene Expression

A. Generation of a Random Oligonucleotide Library (ROL)

The basic structure of the oligonucleotides of each ROL of the present invention is illustrated below [shown below as #1 and SEQ ID NO.:1 (designated N20) and #2 and SEQ ID NO.:2 (designated N24)]. The flanking sequences of said oligonucleotides were designed to be dissimilar to any known plant cis-acting elements. The flanking sequence of each oligonucleotide in each ROL includes a BamHI recognition site for cloning into a vector after isolation of candidate oligonucleotides. The $N_{24}$ ROL (shown below as #1) comprises approximately $2.8 \times 10^{14}$ distinct oligonucleotides. The $N_{20}$ ROL (shown below as #2) comprises approximately $1.1 \times 10^{12}$ distinct oligonucleotides. PCR primers were designed for amplification of ROL (primers N7913 and N8516, shown below as #3 and #4 below, respectively). The tissue-preferred elements of the present invention were 30 isolated from the $N_{20}$ ROL library. Single-stranded synthetic oligonucleotides from the ROL were made double stranded and labeled by standard techniques comprising the use of Klenow fragment, dNTP, and $^{32}$P-dCTP.

Biology Manual" B11:1–22. Gelvin, S. B., Schilperoort, R. A., and Verma, D. P. S. (Eds) Kluwer Acad. Publishers). Briefly, B73 maize seedlings were grown in the greenhouse for 23 days. Root and leaf tissues were harvested and washed with tap water until clean, followed by a wash with double-distilled-water and finally with the homogenizing buffer (25 mM Tris-HCl pH 7.5, 10 mM MgCl, 0.3 M Sucrose, 0.25% (v/v) TRITON X-100, 5 mM beta-mercaptoethanol, 1 mM PMSF). Fresh tissue was homogenized in a Waring blender fitted with new razor blades. 400 ml of cold (4° C.) homogenizing buffer was utilized for every 100 g of tissues. Four pulses of 10 seconds at high speed were given to root tissues. The homogenate was filtered through 2 layers of MIRACLOTH, 1 layer of NYLON msh (120 microns) and finally through a 70 microns nylon mesh. The filtrate was centrifuged in a Sorvall GSA rotor at 3500×g for 15 minutes. The pellet was gently resuspended with a large mouth plastic pipette in 50 ml of the ice cold homogenizing buffer. Nuclei were pelleted at 3500×g for 10 min. The nuclei were washed two more times and stored in 20% glycerol at 80° C. after freezing with liquid nitrogen.

C. Enrichment for Root-specific Oligonucleotides

Figure 2:
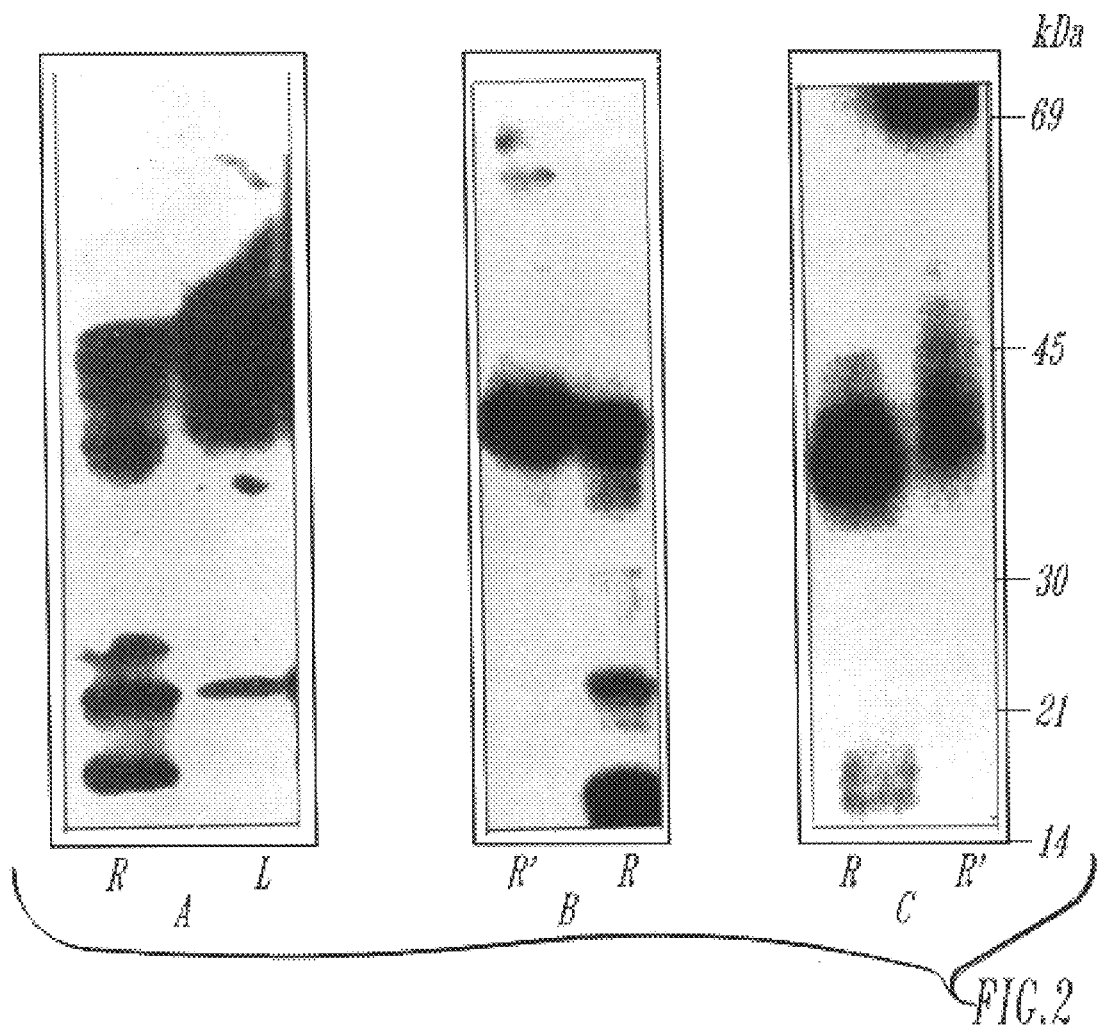
FIG. 2. Panels A, B, and C represent Southwestern blots differentiating oligonucleotides that bind to polypeptides of root tissue nuclear extracts (R and R') and polypeptides that bind to leaf tissue nuclear extracts (L).

A modified version of the Southwestern blot assay based on the method of Miskimins, W. K., et al. (1985. "Use of a protein-blotting procedure and a specific DNA probe to identify nuclear proteins that recognize the promoter region of the transferring receptor gene", Proc. Natl. Acad. Sci. USA 82:6741–6744) was utilized, as schematically shown in FIG. 1. Briefly, both root and leaf protein were separated by 10% SDS-PAGE side by side (30 ug protein/lane). The resultant gel was transferred onto nitrocellulose membrane. The $N_{20}$ ROL was diluted to $10^4$ molecules/ul and labeled by PCR (94° C., 30 sec; 45° C., 1 min; 72° C. 1 min 20 sec; 35 cycles then 72° C., 10 min) in the presence of $\alpha$-$^{32}$P-dCTP and purified on 2% agarose gel. The moiety with which members of an ROL may be labeled include but are not limited to an enzyme, an enzyme substrate, an enzyme cofactor, an enzyme inhibitor, a fluorescent label, a chromophore, a bioluminescer, a specifically bindable ligand such as biotin or a hapten, and radioisotopes including but not limited to $^3$H, $^{14}$C, $^{35}$S, and 125I. The protein blots were probed using the labeled oligonucleotides ($10^8$ cpm/ug) in a binding buffer (10 mM Hepes, pH 7.0 containing 50 mM KCl, 10 mM $MgCl_2$, 1 mM DTT, 0.1 mM EDTA, with 10 ug poly dIdC/ml) for 4 h at RT. The blots were then washed in binding buffer with 3 changes 15 minutes each. Oligonucleotides were observed to bind 14–20 kDa and 30–45 kDa polypeptides of the root extract but not the leaf extract (FIG. 2A). Said oligonucleotides

```
            Bam HI                    Bam HI
#1. 5'GTAAATCTGGATCCGTTG--(N)24--GTTCTGAGGATCCCGTTG 3'      (Seq. ID.1)

Bam HI                    Bam HI
#2. 5'GTAAATCTGGATCCGTTG--(N)20--GTTCTGAGGATCCCGTTG 3'      (Seq. ID 2)

Bam HI
#3. N7913:  5'GTAAATCTGGATCCGTTG 3'                          [SEQ ID NO:3]

Bam HI
#4. N8516:  3'CAAGACTCCTAGGCAAC 5'                           [SEQ ID NO:4]
```

B. Preparation of Nuclear Protein Extracts

The method for isolation of nuclei and preparation of nuclear extracts is modified from that of Green, P. J., et al. (1989. In Vitro DNA Footprinting. In "Plant Molecular were eluted off the membrane by incubating the membrane in 10 mM Tris-1 mM EDTA containing 1.5 M NaCl at 65° C. for 1 hour. Eluted oligonucleotides were recovered by EtOH precipitation with 2 ug of glycogen following a single chloroform extraction. Said eluted oligonucleotides were reamplified, labeled by PCR and used as a probe on a second set of blots containing nuclear extract proteins from root tissue (FIG. 2B). Certain of said eluted oligonucleotides were observed to bind polypeptides in the size range of 30–69 kDa. These oligonucleotides were subsequently eluted, amplified and labeled by PCR. The eluted, labeled oligonucleotides were then used as a probe for a third set of nuclear protein blots (FIG. 2C) and were observed to bind to 69 kDa, 36 kDa and 30–45 kDa polypeptides. Bound oligonucleotides were recovered individually, PCR amplified and ligated into a TA cloning vector (Clontech). Following cloning into the TA vector, both strands of said oligonucleotides were then sequenced using an ABI 373 Automate DNA Sequencer.

E. Isolation of the Seq6 and MinSeq6 Root-tissue Preferred Promoter Elements

A novel DNA sequence, Seq6, was isolated using the above-described methodologies (shown as #5 below and SEQ ID NO. 5).

5. Seq6: 5'GGATCCTCAGAACACGCAAGTTGC-
CAGCTCACCCAACGGATCC 3'

A maize promoter element that confers root-preferred gene expression has not been identified nor utilized in any synthetic promoter expression vectors reported in prior art. Relatively short promoter elements such as Seq6 or its derivative are amenable to alterations, multimerizations, etc., thus improving experimental controls which is not easily performed on large promoter sequences previously identified in many plant species. The previously described promoters must be subjected to a mutational or differential analysis to define the relatively short promoter elements that confer gene regulation.

F. Bandshift Assays

Bandshift assays were carried out according to McKendree et al. (1990. Plant Cell 2:207–214). Each reaction contained 1 ug of poly(dIdC), 2 ug tRNA and 50 mM KCl. In competition bandshift studies, a 200-fold excess of competitor DNA was first mixed with the nuclear extracts followed by the addition of the probe. Samples were separated by electrophoresis in 5% native polyacrylamide gels at 30 mA for approximately 1.5 hours. The gels were fixed in solution containing 20% ethanol and 5% acetic acid for 20 min and dried under vacuum. Dried gels were exposed to BTM film at –80° C. overnight with an intensifier screen.

Figure 3:
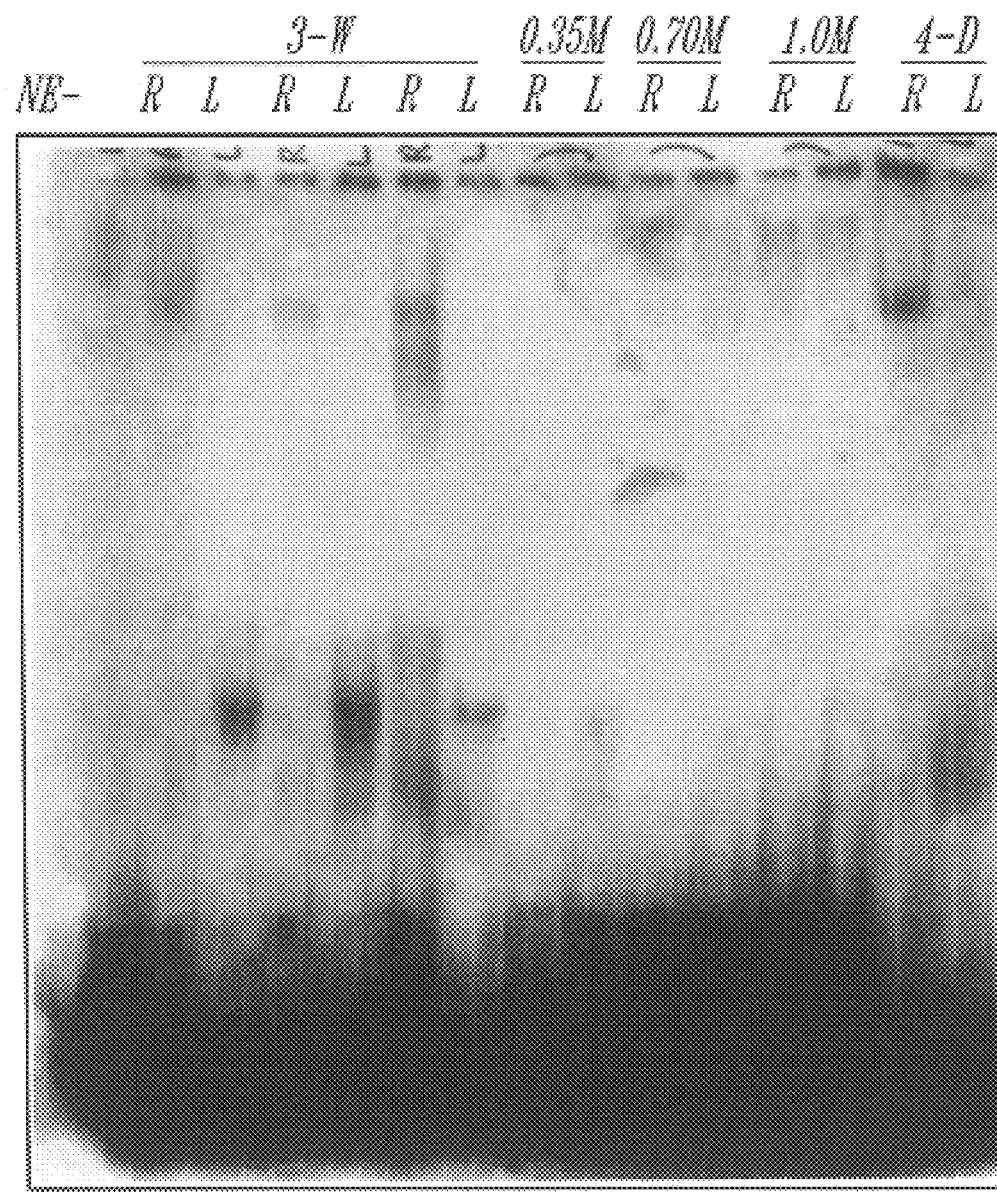
FIG. 3. Bandshift assay using nuclear extracts from 3-week old (3-W) or 4-day old tissues (4-D) demonstrating that Seq6 interacts with distinct factors in root tissue that are not present in leaf tissue.
Figure 4:
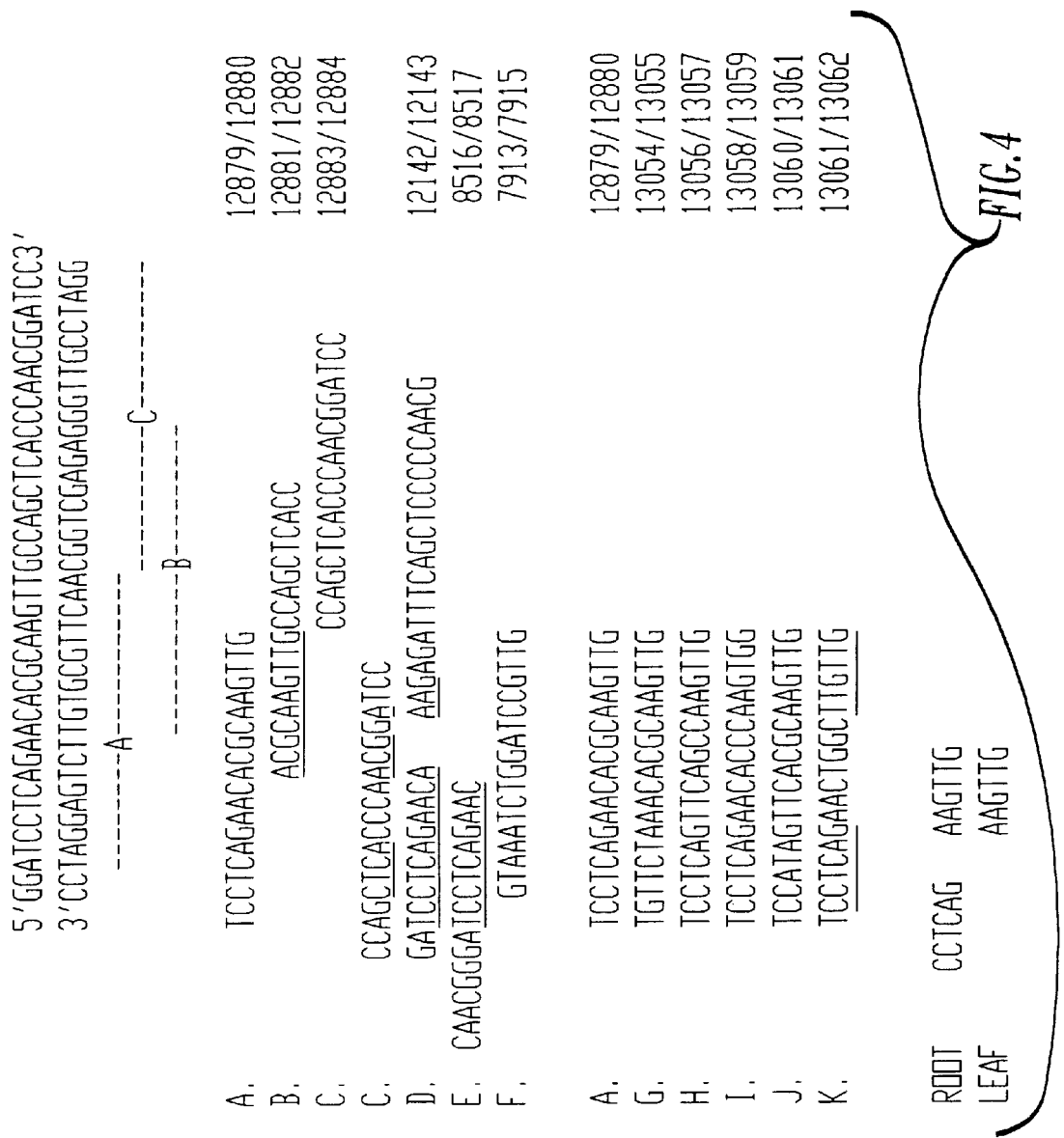
FIG. 4. Competitors utilized to identify the minimal sequence of Seq6 that determines binding to root tissue nuclear extracts.
Figure 5:
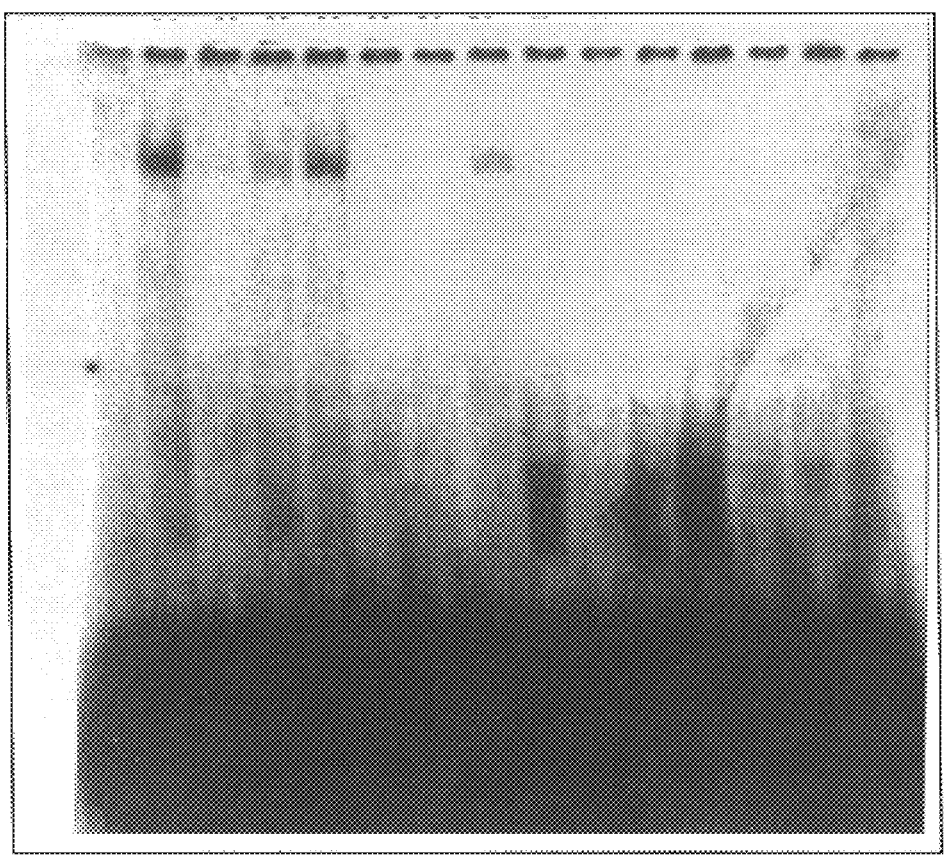
FIG. 5. Demonstration that the approximate 5' half of Seq6 specifically binds to nuclear factors of root tissue (R) distinct from those of leaf tissue (L) isolated from 3-wk old (3-W) plants. Competitors utilized are indicated and are labeled as in FIG. 4.
Figure 6:
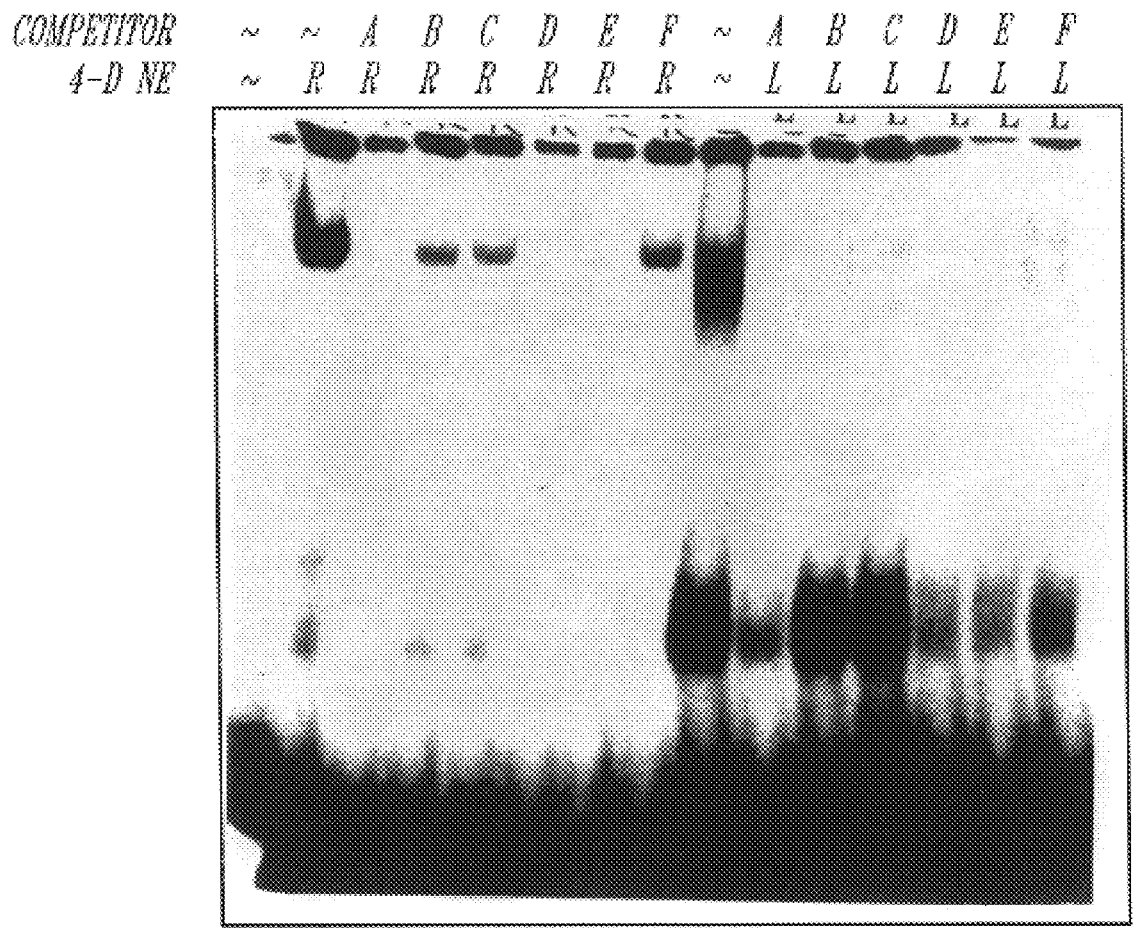
FIG. 6. Demonstration that the approximate 5' half of Seq6 specifically binds to nuclear factors of root tissue (R) distinct from those of leaf tissue (L) isolated from 4 day old (4-D) plants. Competitors utilized are indicated and are labeled as in FIG. 4.
Figure 7:
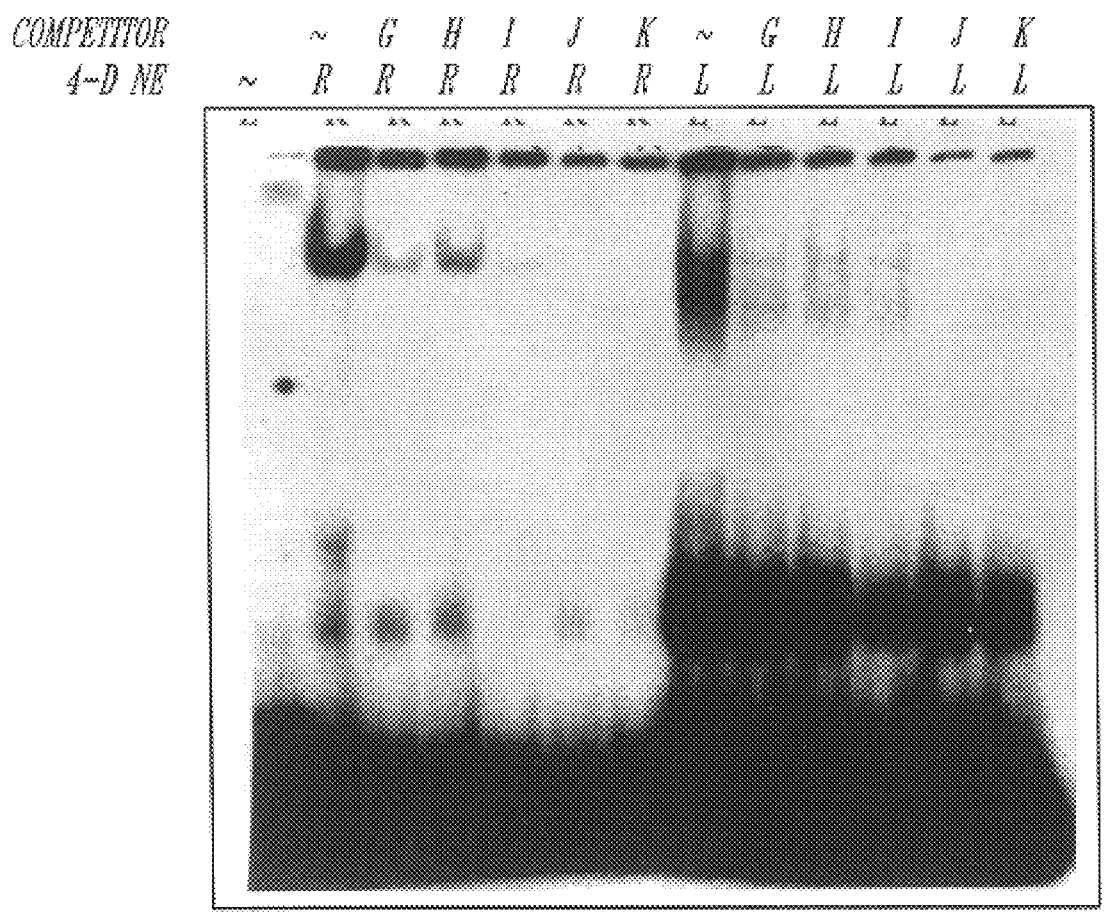
FIG. 7. Demonstration that the approximate 5' half of Seq6 specifically binds to nuclear factors of root tissue (R) distinct from those of leaf tissue (L) isolated from 4 day old (4-D) plants. Competitors utilized are indicated and are labeled as in FIG. 4.

Bandshift assays using nuclear extracts from 3-week old or 4-day old tissues demonstrate that Seq6 interacts with a distinct factor(s) from root nuclear extracts that are not present in leaf nuclear extracts (FIG. 3). The minimal sequence of Seq6 was determined using a series of competitor experiments that are illustrated in FIG. 4. It was demonstrated that the approximate 5'-half of Seq6 specifically binds to factors present in root tissue distinct from those present in leaf tissue (3-wk nuclear extracts, FIG. 5; 4-d nuclear extracts, FIGS. 6 and 7) resulting in the identification of minSeq6 (as shown in #6 below and in SEQ ID NO. 6).

6. minSeq6: 5'TCCTCAGAACACGCAAGTTGCC 3'

Figure 8:
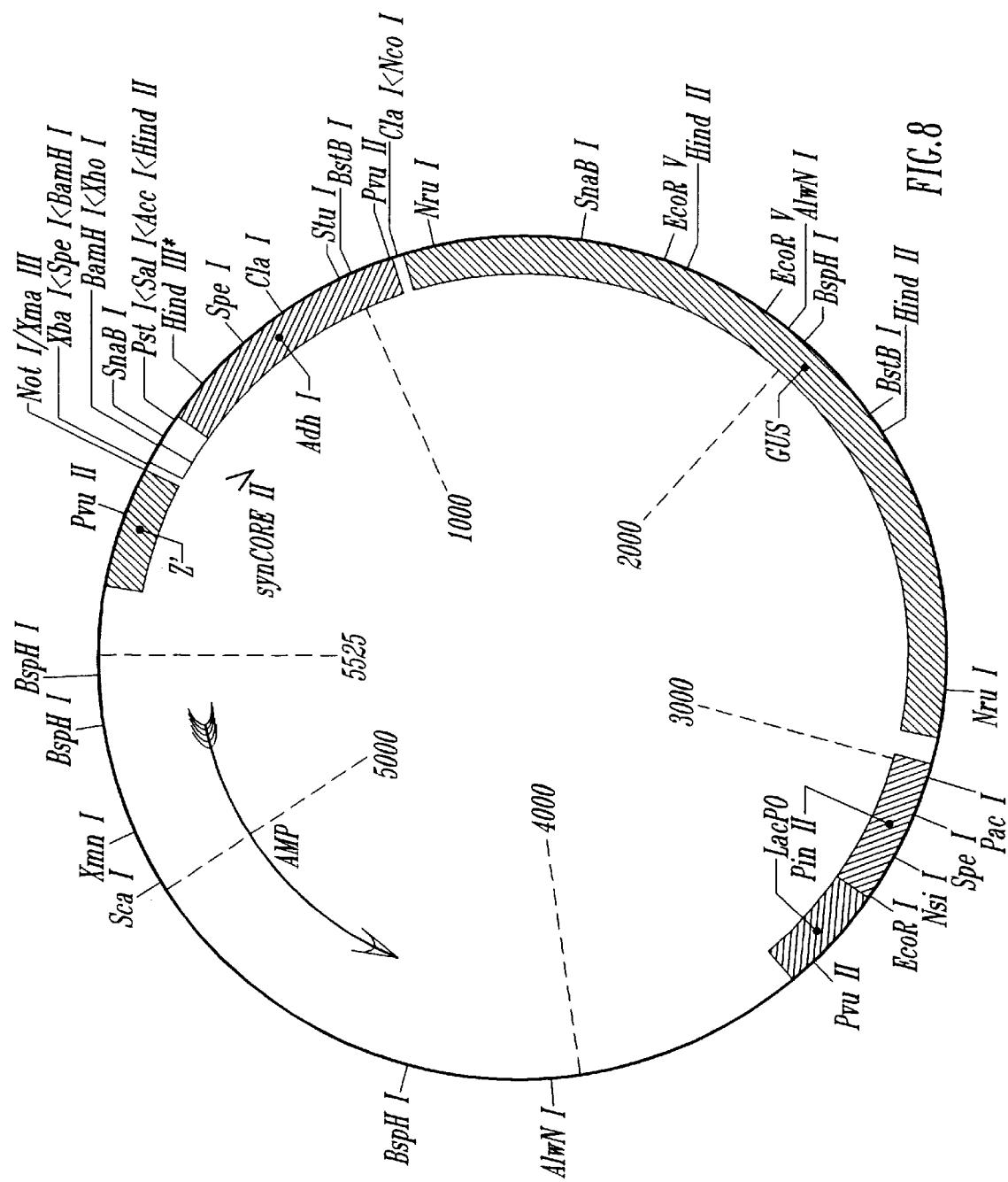
FIG. 8. Map of plasmid PHP8880 comprising the Seq6 root-preferred transcriptional regulatory element (S6) operably linked to the GUS reporter gene.
Figure 9:
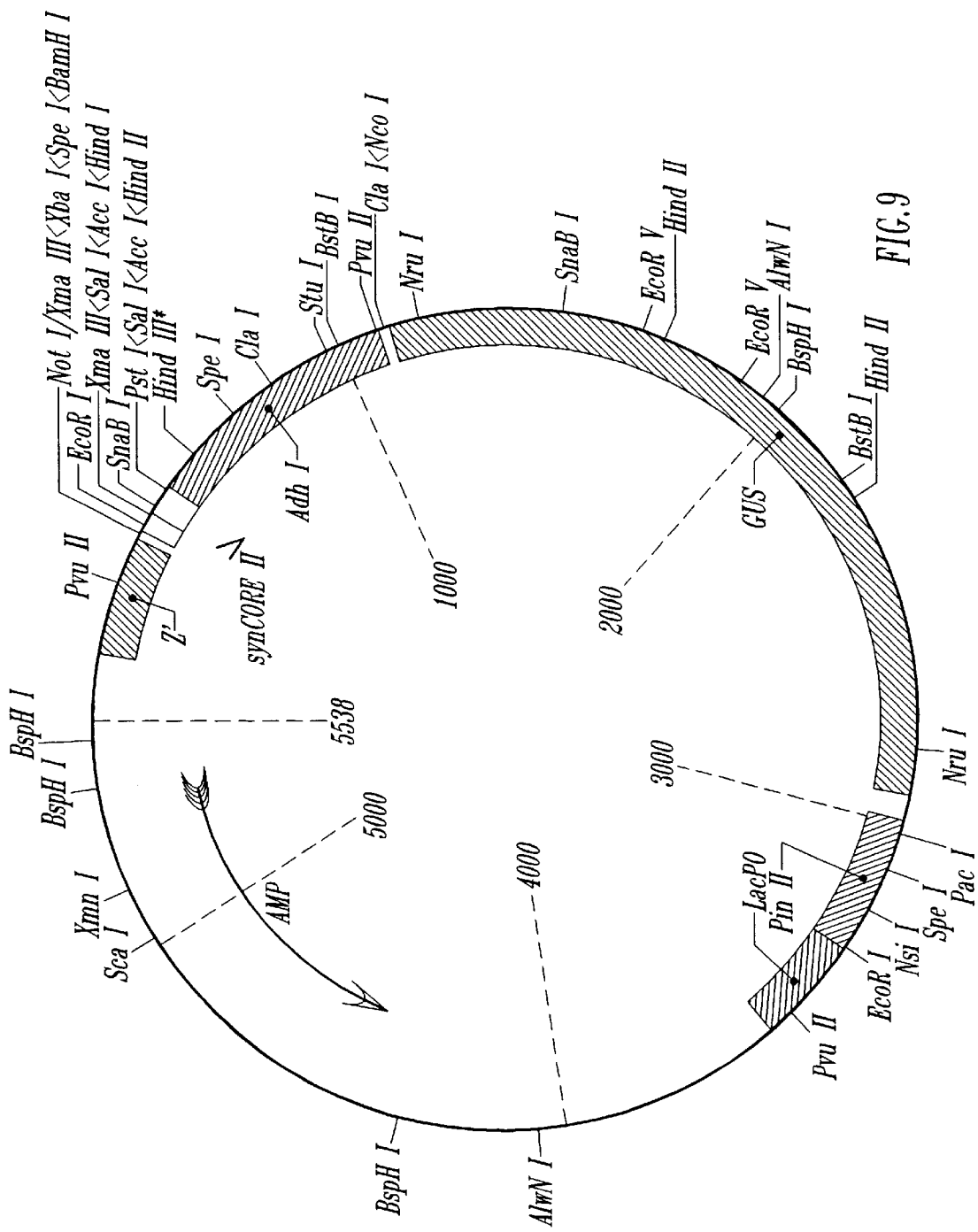
FIG. 9. Map of plasmid PHP8887 comprising the Seq22 element (S22) operably linked to the GUS reporter gene.
Figure 10:
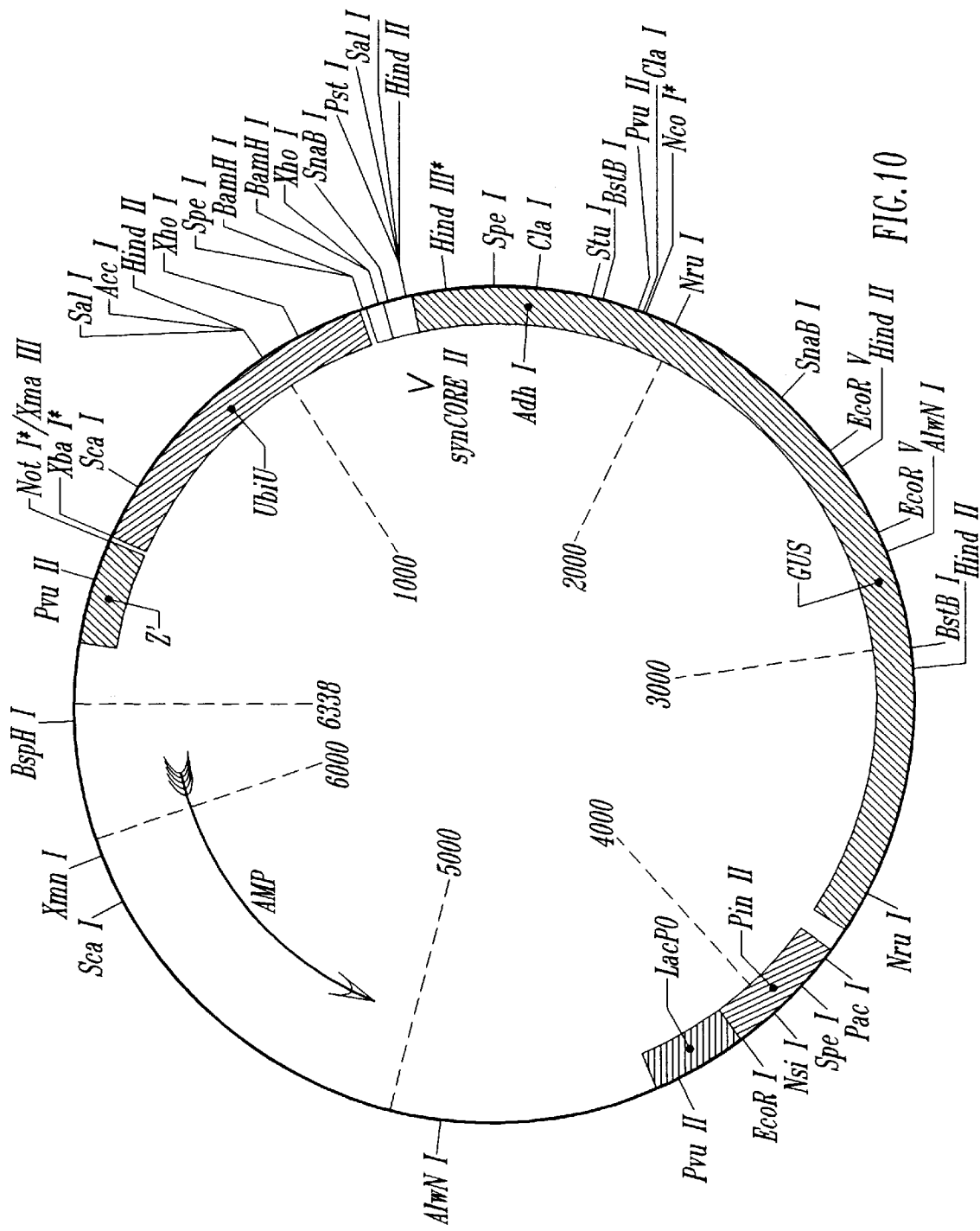
FIG. 10. Map of plasmid PHP8888 comprising the Seq6 root-preferred transcriptional regulatory element (S6) downstream of the Ubi-1 enhancer element (UbiU), said Seq6 root preferred transcriptional regulatory region being operably linked in cis to the GUS reporter gene.

EXAMPLE 2
Seq6-driven Root-preferred Gene Expression
A. Seq6 Expression Vector Construction The seq6 element was tested for the ability to direct tissue-preferred gene expression by incorporation into expression vectors and transfection of said expression vectors into plant tissues. The oligonucleotides were cloned into the TA cloning vector and PCR-amplified using T7 and Sp6 primers. The PCR products were digested with BamHI and the ~40 bp DNA fragments were isolated from a 1% agarose gel. These 40 bp fragments comprising Seq6 or Seq22 were ligated into either a BamHi-digested DP6341 vector (FIG. 8) or a BamHI-digested DP 9342 vector that contains the ubi-1 enhancer and the synCORE minimal promoter sequence driving an AdhI::GUS::PinII gene. In the expression vectors comprising the Seq6 or Seq22 elements, said elements are positioned between the ubi-1 enhancer and the synCORE minimal promoter element. A negative control plasmid comprising the Seq22 element operably linked to the GUS reporter gene is illustrated in FIG. 9. The enhancer region (-865- to -54) of the maize ubiquitin 1 promoter (ubi-1) was cloned upstream of the Seq6 element in the plasmid PHP8880 (FIG. 10) or the Seq22 element (control) in the plasmid PHP8887 to improve the basal level of gene expression. The resultant plasmids comprising the ubi-1 enhancer upstream of either the Seq6 or Seq22 potential tissue-specific transcriptional elements are designated UbiEnh.-Seq6-SynCore::GUS (PHP8888) or and UbiEnh.-Seq22-SynCore::GUS (PHP8889), respectively. Pertinent sequences of these GUS vectors were confirmed by endonuclease restriction mapping and DNA sequencing.

B. Transient Assays

Seeds from two maize inbreds, B73 and W22 Stadler, were surface sterilized by immersion in bleach for 1 min followed by several washes with sterile water and planting on moistened 20 lb weight germination papers followed by incubation at 26° C. in the dark. Three-day-old seedlings were used as targets for particle bombardment transformation and assayed for luciferase (LUC) activity essentially as described by Klein, et al. (1989. Proc Natl. Acad. Sci. USA 86: 6681–6685). Six ug of the CRC reporter gene (a chimeric DNA-binding factor derived from the maize C1 and R gene product) was co-precipitated with 3 ug of target gene Bz1::LUC and 1 ug of the positive control plasmid, DP3953 (Ubi-Ubi::GUS) onto tungsten particles. In this assay, luciferase activity (from the Bz1::LUC plasmid) is an indirect measure of activity of the CRC constructs. Eight ug of the GUS reporter plasmid was co-precipitated with 2 ug of the internal control, PHP4992 (Ubi-Ubi::LUC) onto tungsten particles. Following transfection, GUS activity was measured using the GUS-Light™ kit (TROPIX) according to the manufacturer's protocol. Whole seedlings were bombarded and 1.5 cm shoot as well as root tissues were harvested individually following a 20 h incubation at 26° C. The harvested tissues were homogenized in 200 ul of 100 mM potassium phosphate [pH7.8], lmM EDTA. After spinning at 4000 rpm for 30 min, the supernatant was used directly for both GUS and LUC assays. Gene promoter activity was expressed as LUC/GUS/2 ul extracts or GUS/LUC/2 ul extracts depending on the test construct.

Figure 11:
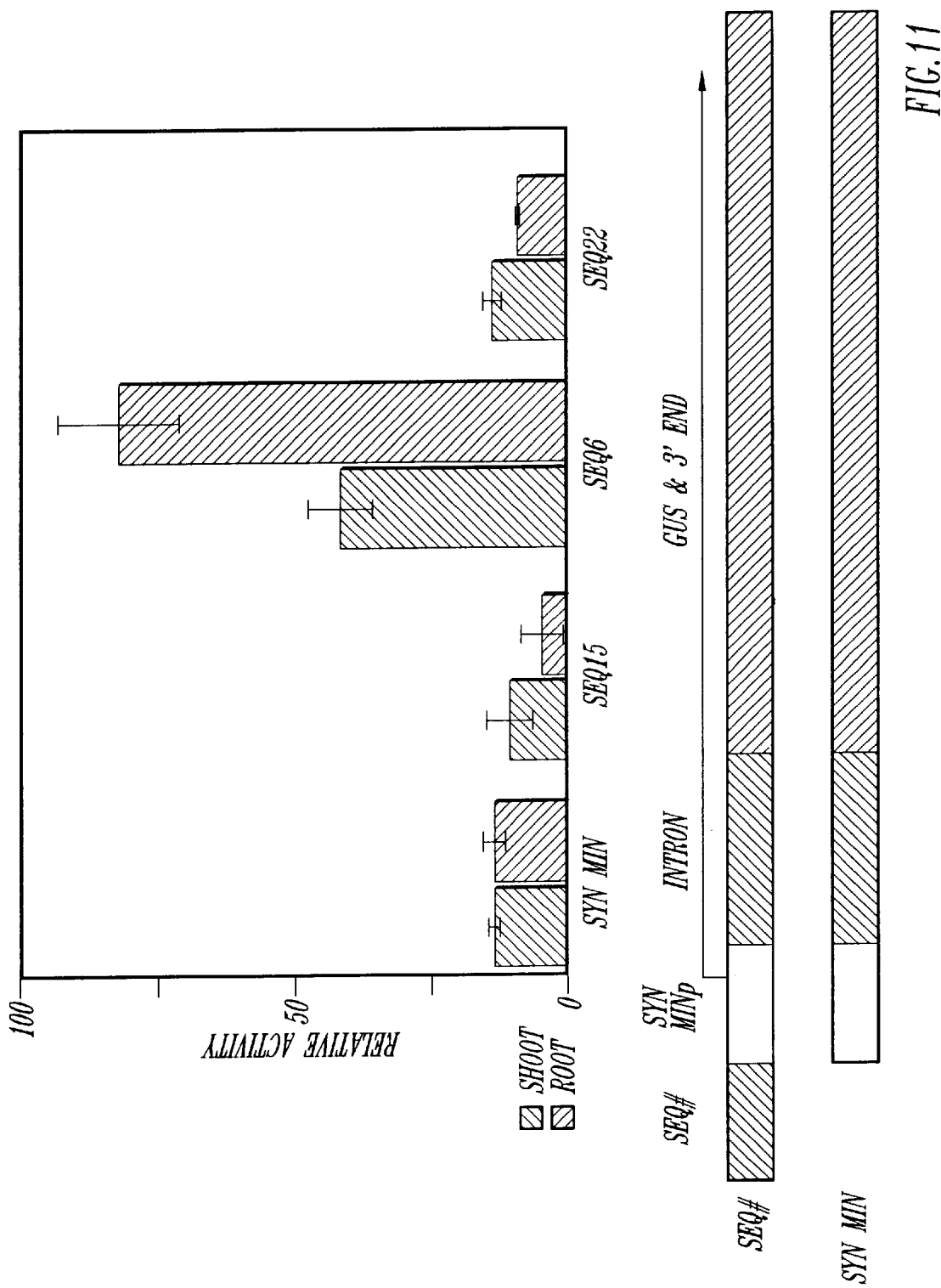
FIG. 11. SEQ#::GUS Transient Assays in 4-Day Old Maize Seedlings. Root-preferred GUS gene expression driven by the Seq6 transcriptional regulatory element is demonstrated. Data generated using negative control plasmids (SynMin, Seq15 and Seq22) is included.
Figure 12:
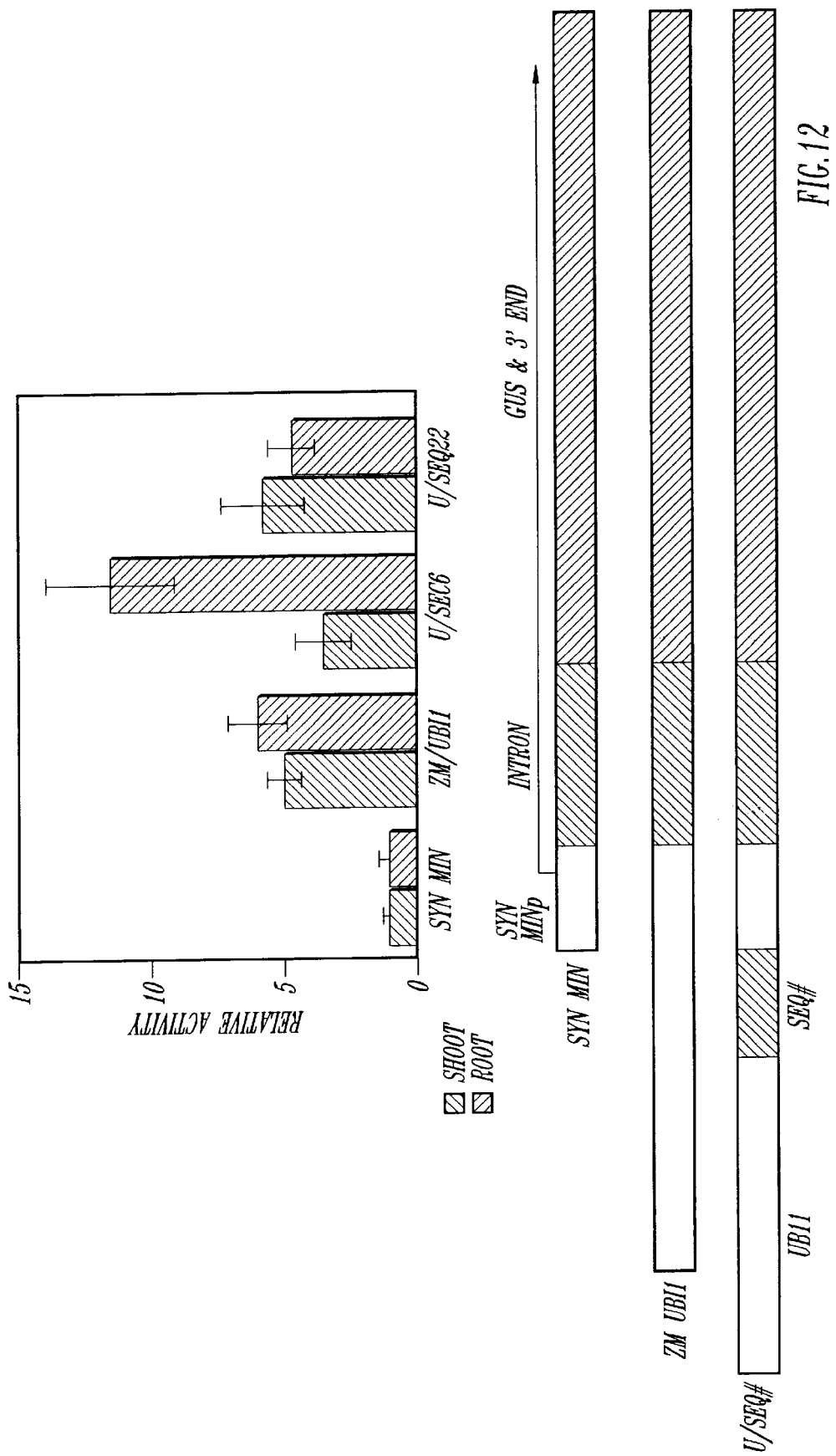
FIG. 12. UBI/SEQ#::GUS Transient Assays in 4-Day Old Maize Seedlings. Root-preferred GUS expression in four day old maize seedlings driven by the Seq6 transcriptional regulatory elements (U/Seq6). Negative control plasmids include SynMin, Zm Ubi1 and U/Seq22.

The novel sequence element Seq6 was observed to drive high levels of root-preferred expression of both GUS and CRC in transient assays (FIG. 11). Control sequence elements such as Seq15 and Seq22 did not alter expression levels. Importantly, the activity levels of the Seq6-based expression vector was increased 100-fold by addition of the ubiquitin enhancer element upstream (2-fold above the ubi-1 promoter alone) while maintaining its preference for root expression. Root-preferred expression of GUS driven by the promoter containing the Seq6 element (designated U/Seq6) is fuirther demonstrated in FIG. 12. The data indicates that the Seq6 DNA element is useful in conjunction with a minimal promoter in driving expression of a gene in a root-preferred manner.

EXAMPLE 3
Root-tissue Preferred Gene Expression in Transgenic Plants

It is necessary to demonstrate that said root-tissue preferred transcriptional regulatory elements drive gene expression in a tissue-preferred manner in vivo. A model system that allows for testing of potential root-tissue preferred gene expression vectors is the development of transgenic maize. An expression vector comprising potential root-tissue preferred transcriptional regulatory sequences operably linked to a GUS reporter gene are used to stably transform regenerable maize cultures via the particle gun bombardment method. The method utilized for transfection of various types of plant cells or plant tissues may further include but are not limited to liposome-mediated transfection, calcium phosphate-mediated transfection, bacterial- or viral-mediated gene transfer, or electroporation A second vector, carrying a selectable marker gene behind a promoter that demonstrates activity in plants is co-bombarded and used to select for transformed events. Immediately after bombardment, culture events are incubated at 27° C. in the dark for 6 days followed by transfer to selective media containing 3 mg/L bialophos (Meiji Seika, Japan). About 6 weeks later putative transformed colonies are transferred onto regeneration media. After several weeks, developing embryos or scutellar structures are transferred and cultured separately in the light and transgenic maize plantlets are recovered.

Following regeneration of plantlets in test tubes from callus cultures, four seedlings of each event are stained in McCabe's stain to select positive events to take to the greenhouse. For all events that exhibit GUS staining in seedlings, sibling plants are potted and grown to maturity in the greenhouse. Following regeneration of up to 15 transgenic (T0) plants per event, ears are pollinated and allowed to mature in the greenhouse. At 5–9 days after pollination (dap), samples from various regions of the plant including the root tissue and at least one non-root tissue are collected and processed. For visual analysis of promoter activity, the plant tissues from transgenics are incubated for 18–36 hours in McCabe's stain. Small segments of maize tissues are ground, spun, frozen in liquid nitrogen, and used for quantitative GUS assays via the GUS-Light™ chemiluminescent detection system using conditions and solutions specified by the manufacturer (Tropix, Inc., Bedford, Mass.). Total soluble protein concentrations are measured using methods well known to those skilled in the art. Samples of extract of at least two samples of tissue collected from two plants of each event are used for each determination. GUS expression is illustrated as ng GUS/mg protein (ppm) and plotted for all transgenic events analyzed. T1 seed collected from sibling plants allowed to complete development are grown to maturity in the greenhouse, and samples are collected and analyzed again as for the T0 plants.

In all positive seedling events stained with McCabe's stain and observed visually, prominent GUS expression is observed primarily in the root tissue. The GUS-Light™ chemiluminescence detection system and the BCA protein assay are used subsequently to quantitate the amount of GUS protein expression in the different tissues. Variation in expression levels between events is observed, as is typically observed in plant transformation experiments utilizing methods such as particle gun bombardment. This variation may be attributable to multiple or varying integration sites (position effects), DNA rearrangement during integration, or event-specific transgene quieting or instability. The data indicates that the potential root-tissue preferred transcriptional regulatory element drives root-tissue preferred gene. Thus, transcriptional regulatory elements are defined that direct root-tissue preferred gene expression in planta.

EXAMPLE 4
Root-tissue Preferred Expression of Effector Genes that Confer a Selective Advantage to Maize Root-tissue preferred gene expression offers utility where it is desirable not to have strong expression of transgenes in all plant tissues. Additionally, higher levels of expression, such as with the CaMV 35S promoter or the maize ubiquitin promoter (Christensen et al., 1992), may not be required or desired in certain applications, as with expression of highly efficacious [e.g., cryIA(b)] or potentially cytotoxic (e.g., RNAase) gene products. Root-tissue preferred transcriptional regulatory elements provide a suitable alternative for expressing genes in plants. Root-preferred gene expression provides several advantages to a plant including but not limited to alteration of the growth rate or function of the root tissue, resistance to root-preferred pathogens, pests, herbicides or adverse weather conditions as well as broadening the range of soils or environments in which said plant may thrive. Root-preferred gene expression would also provide a mechanism by which root morphology and metabolism may be altered to improve yield (i.e., direct expression of transporter proteins). Further advantages to root-preferred gene expression include the production of useful proteins in an industrial setting. Advantages include but are not limited to the production of light-sensitive proteins in root tissue such that said proteins are not exposed to light.

An example includes delivery of a corn rootworm (CRW) resistance gene and thus limiting expression to tissues necessary for CRW control. An expression vector comprising transgene comprising a root-tissue preferred transcriptional regulatory element operably linked to a CRW-resistance gene is transfected into callus cultures of maize. A second vector comprising a selectable marker is also transfected into said callus cultures to provide a method for selection of transformed cells. Transfection and isolation of transformed cells including expansion and growth into mature transgenic plants is performed. Following identification of those transformed plants harboring said transgene, plants are challenged by exposure to the corn rootworm. Plants expressing the CRW-resistance gene in root tissues are resistant to challenge by the corn rootworm. Thus, said root-tissue preferred transcriptional regulatory element provides a tool with which root-preferred gene expression of an effector gene confers a selective advantage upon a plant.

The present invention represents a significant improvement in the methodology utilized in the isolation and utilization of tissue-preferred promoter elements. The present invention is considered important and novel to those skilled in the art. Said invention provides a rapid means of identifying promoter elements for a number of regulated expression needs by circumventing the lengthy cloning, characterization and promoter dissection techniques of the prior art. Furthermore, the methodology of this invention is applicable to any organism or tissue from which nuclear extracts may be prepared and is not in any way limited to identification of plant tissue-preferred transcriptional elements. While a preferred form of the invention has been shown in the drawings and described, since variations in the preferred form will be apparent to those skilled in the art, the invention should not be construed as limited to the specific form shown and described, but instead is as set forth in the claims.

What is claimed is:

1. A method for identifying transcriptional regulatory elements capable of regulating a root tissue gene transcription in a maize plant comprising the steps of:
    (a) amplifying an aliquot from a random deoxyribonucleotide library in the presence of a labeling moiety to provide a population of labeled amplified deoxyribonucleotides;
    (b) contacting said labeled deoxyribonucleotides with a crude nuclear protein extract from maize root tissue, displayed on a solid support, under conditions allowing for formation of a complex between the proteins of said crude nuclear protein extract and said labeled deoxyribonucleotides;
    (c) simultaneously or subsequently performing step (b) with a crude nuclear protein extract from maize tissue other than root tissue;
    (d) comparing the complexes formed in step (b) and (c) and selecting complexes that are formed in step (b) but not in step (c);
    (e) recovering the labeled deoxyribonucleotides from the selected complexes; and
    (f) individually integrating the deoxyribonucleotides from step (e) into an expression vector and identifying those deoxyribonucleotides capable of regulating a root tissue gene transcription.

2. The method of claim 1 wherein the random deoxyribonucleotide library is generated using nucleotide sequences selected from the group consisting of SEQ ID NO: 1 and SEQ ID NO: 2.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
       (A) LENGTH: 60 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "oligonucleotide"

(ix) FEATURE:
       (A) NAME/KEY: misc_feature
       (B) LOCATION: 1..60
       (D) OTHER INFORMATION: /product= "N24"

(xi) SEQUENCE DESCRIPTION: SEQ ID NO:1:

GTAAATCTGG ATCCGTTGNN NNNNNNNNNN NNNNNNNNNN NNGTTCTGAG GATCCCGTTG      60

(2) INFORMATION FOR SEQ ID NO:2:

(i) SEQUENCE CHARACTERISTICS:
       (A) LENGTH: 56 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "oligonucleotide"

(ix) FEATURE:
       (A) NAME/KEY: misc_feature
       (B) LOCATION: 1..56
       (D) OTHER INFORMATION: /product= "N20"

(xi) SEQUENCE DESCRIPTION: SEQ ID NO:2:

GTAAATCTGG ATCCGTTGNN NNNNNNNNNN NNNNNNNNGT TCTGAGGATC CGTTG      56

(2) INFORMATION FOR SEQ ID NO:3:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "oligonucleotide"

(ix) FEATURE:
       (A) NAME/KEY: misc_feature
       (B) LOCATION: 1..18
       (D) OTHER INFORMATION: /product= "N7913"

(xi) SEQUENCE DESCRIPTION: SEQ ID NO:3:

GTAAATCTGG ATCCGTTG      18

(2) INFORMATION FOR SEQ ID NO:4:

(i) SEQUENCE CHARACTERISTICS:
       (A) LENGTH: 17 base pairs
       (B) TYPE: nucleic acid
       (C) STRANDEDNESS: single
       (D) TOPOLOGY: linear

```
    (ii) MOLECULE TYPE: other nucleic acid
        (A) DESCRIPTION: /desc = "oligonucleotide"

(ix) FEATURE:
        (A) NAME/KEY: misc_feature
        (B) LOCATION: 1..17
        (D) OTHER INFORMATION: /product= "N8516"

(xi) SEQUENCE DESCRIPTION: SEQ ID NO:4:

CAAGACTCCT AGGCAAC                                                          17

(2) INFORMATION FOR SEQ ID NO:5:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(ix) FEATURE:
        (A) NAME/KEY: misc_feature
        (B) LOCATION: 1..43
        (D) OTHER INFORMATION: /product= "Seq6"

(xi) SEQUENCE DESCRIPTION: SEQ ID NO:5:

GGATCCTCAG AACACGCAAG TTGCCAGCTC ACCCAACGGA TCC                             43

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(ix) FEATURE:
        (A) NAME/KEY: misc_feature
        (B) LOCATION: 1..22
        (D) OTHER INFORMATION: /product= "minSeq6"

(xi) SEQUENCE DESCRIPTION: SEQ ID NO:6:

TCCTCAGAAC ACGCAAGTTG CC                                                    22

(2) INFORMATION FOR SEQ ID NO:7:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GGATCCTCAG AACACGCAAG TTGCCAGCTC ACCCAACGGA TCC                             43

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:8:

TCCTCAGAAC ACGCAAGTTG                                      20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ACGCAAGTTG CCAGCTCACC                                      20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CCAGCTCACC CAACGGATCC                                      20

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GATCCTCAGA ACAAAGAGAT TTCAGCTCCC CCAACG                    36

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CAACGGGATC CTCAGAAC                                        18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GTAAATCTGG ATCCGTTG                                        18

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

TGTTCTAAAC ACGCAAGTTG                                                       20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

TCCTCAGTTC AGCCAAGTTG                                                       20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

TCCTCAGAAC ACCCAAGTGG                                                     20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TCCATAGTTC ACGCAAGTTG                                                     20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

TCCTCAGAAC TGGCTTGTTG                                                     20

(2) INFORMATION FOR SEQ ID NO:19:

-continued

```
(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:19:

CCTCAGAAGT TG                                                          12
```